United States Patent [19]

Longo et al.

[11] Patent Number: 4,990,635

[45] Date of Patent: Feb. 5, 1991

[54] SYNTHESIS OF 6-METHYLENE DERIVATIVES OF ANDROSTA-1,4-DIENE-3,17-DIONE

[75] Inventors: Antonio Longo; Paolo Lombardi, both of Milan, Italy

[73] Assignee: Farmitalia Carlo Erba S.r.l., Milan, Italy

[21] Appl. No.: 294,016

[22] Filed: Jan. 6, 1989

[51] Int. Cl.$^5$ .............................................. C07J 1/00
[52] U.S. Cl. .................................................... 552/526
[58] Field of Search ...................................... 260/397.3

[56] References Cited

U.S. PATENT DOCUMENTS

| | | | |
|---|---|---|---|
| 3,112,305 | 11/1963 | Kirk | 260/239.55 |
| 4,322,349 | 3/1982 | Annen et al. | 260/239.55 |
| 4,416,821 | 11/1983 | VanRheenen | 260/347.3 |
| 4,512,986 | 4/1985 | Reel et al. | 514/170 |
| 4,808,616 | 2/1989 | Buzzett | 514/177 |

FOREIGN PATENT DOCUMENTS

3338212A1  4/1985  Fed. Rep. of Germany .

OTHER PUBLICATIONS

Carey and Sundberg, A duanced Organic Chemistry 2nd Ed. Part B pp. 44–46 (1983).
Annen et al, Synthesis, 1: 34–40, 1982.
Annen, Klaus et al. "A Simple Method for 6-Methylenation of 3-Oxo-Δ$^4$-steroids," *Synthesis*, pp. 34–42.
Burn, D. et al. "Modified Steroid Hormones-XXXIII[1]; Steroidal 6-Formyl-3-Alkoxy-3, 5-Dienes and Some of Their Transformations," *Tetrahedron*, vol. 20, (1964), pp. 597–609.

*Primary Examiner*—Robert Gerstl
*Attorney, Agent, or Firm*—Armstrong, Nikaido, Marmelstein, Kubovcik & Murray

[57] ABSTRACT

The invention relates to a new process for the preparation of known aromatase inhibitors of the following formula (I)

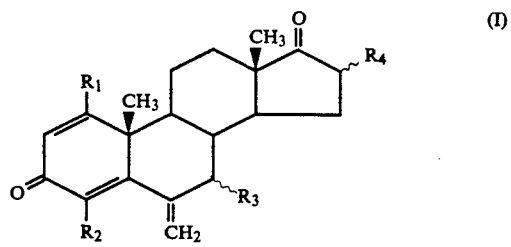

wherein
each of $R_1$ and $R_3$, independently, is hydrogen or $C_1$-$C_6$ alkyl;
$R_2$ is hydrogen, halogen or $C_1$-$C_6$ alkyl; and
$R_4$ is hydrogen or fluorine;
the process comprising submitting to Mannich reaction a compound of formula (II)

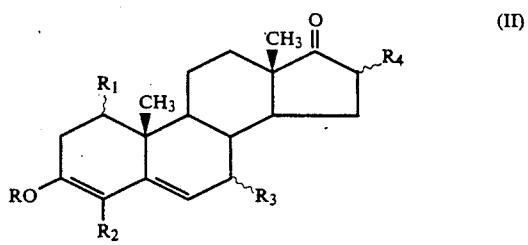

wherein
$R_1$, $R_2$, $R_3$ and $R_4$ are as defined above and R is a lower alkyl group, and then dehydrogenating the respective 6-methylene-3-oxo-Δ$^4$-steroid derivative thus obtained, by methods known per se.

2 Claims, No Drawings

SYNTHESIS OF 6-METHYLENE DERIVATIVES OF ANDROSTA-1,4-DIENE-3,17-DIONE

The introduction of a methylene, i.e. $CH_2=$ group at the 6-position of 3-oxo-$\Delta^4$-steroids is a well known process in the art. This type of substitution has been previously achieved by procedure involving a many steps synthesis. The method described by D. Burn et al. in Tetrahedron 20, 597 (1964), for instance, requires the initial conversion of a 3-oxo-$\Delta^4$-steroid into its 3,5-dienol ether, which is then subjected to Vilsmeier conditions (phosphoryl chloride/dimethylformamide) to yield the iminium salt. After hydrolysis, reduction, and dehydration, the 6-methylene derivative is obtained: Scheme A.

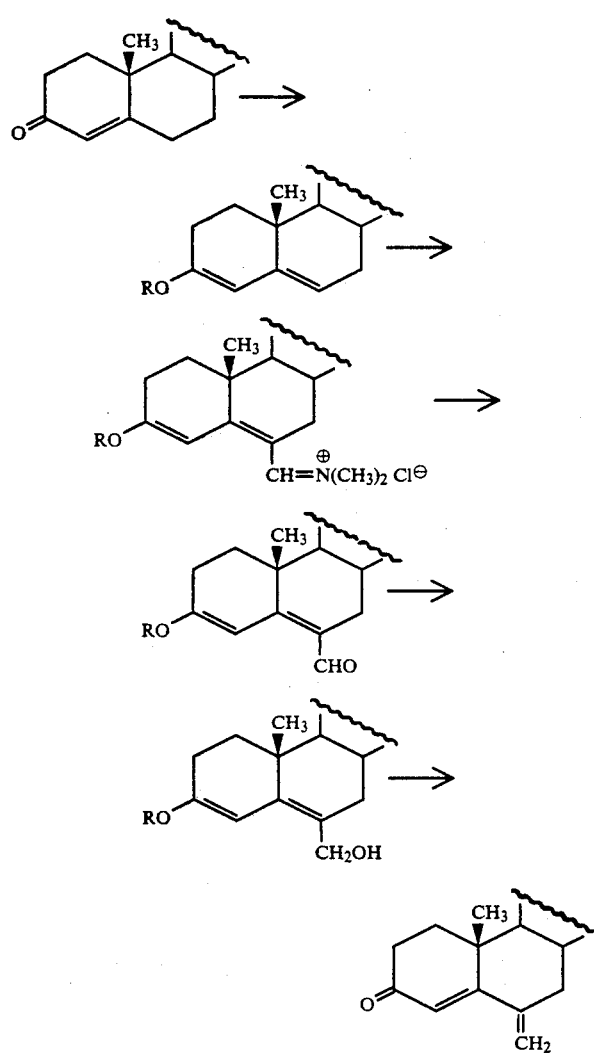

wherein R is lower alkyl.

Published British patent application No. 2177700 and copending European patent application No. 87306125.3 disclose 6-methylene derivatives of androsta-1,4-diene-3,17-dione, which are inhibitors of the biotransformation of endogenous androgens to estrogens, i.e. they are aromatase inhibitors. These compounds are useful, e.g., in the treatment of hormone-dependent tumours such as breast, endometrial and ovarian cancers.

In these British patent applications the methylenation step synthesis is carried out according to the method of K. Annen et al. described in Synthesis 1982,34: Scheme B.

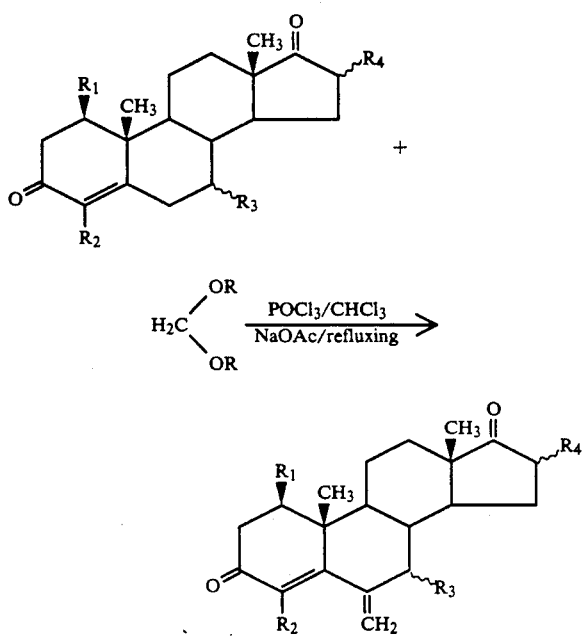

wherein
each of $R_1$ and $R_3$, independently, is hydrogen or $C_1$-$C_6$ alkyl;
$R_2$ is hydrogen, halogen or $C_1$-$C_6$ alkyl;
$R_4$ is hydrogen or fluorine; and R is a lower alkyl group.

The use of formaldehyde acetals with longer or branched alkoxy groups results in a lower yield of product. Although this method for direct methylenation of 3-oxo-$\Delta^4$ steroids provides an economical method for the introduction of a 6-methylene group, it is not possible to obtain yields of products higher than about 40-45%.

Furthermore, if the whole process for the preparation of the corresponding 6-methylenandrosta-1,4-diene-3,17-diones, described in the above-mentioned British patent applications, is considered, it has to be noticed that:

a. The obtained 3-oxo-6-methylene-$\Delta^4$-steroids require to be submitted to a long-lasting column chromatography purification, before being dehydrogenated to the corresponding 6-methylene-$\Delta^{1,4}$-derivatives.
b. The best oxidizing agent used in the dehydrogenation step synthesis is dichlorodicyanobenzoquinone (DDQ), that is very expensive.
c. The dehydrogenation step synthesis provides yields of end-products not higher than about 40-50%.
d. The obtained end-products require a further long-lasting column chromatography purification.

Hence the process described in the above-mentioned patent applications provides yields of about 20-25% of end-products. It requires two long-lasting column chromatography separations; and what is the more the best reducing agent, i.e. DDQ, is very expensive. It appears clear that this process cannot be advantageously used for large-scale production. In investigating both different methods and different intermediate products for preparing compounds described in the above-mentioned British applications and having the following formula (I)

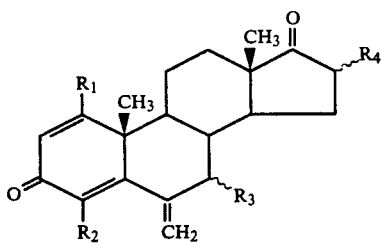

(I)

wherein $R_1$, $R_2$, $R_3$ and $R_4$ are as defined above, a very interesting observation was made in the case of 3,5-dienol ethers of the following general formula (II)

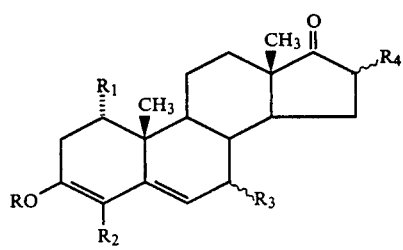

(II)

wherein R, $R_1$, $R_2$, $R_3$ and $R_4$ are as defined above. They can be indeed subjected to Mannich reaction, thus providing the respective 6-methylene-3-oxo-$\Delta^4$-steroid derivatives, which in their turn can be easily converted into the respective compounds of formula (I) through a simple procedure.

In the formulae of the specification the heavy solid line (◂) indicates that a substituent is in the $\beta$-configuration, i.e. above the plane of the ring; a dotted line (..........) indicates that a substituent is in the $\alpha$-configuration, i.e. beneath the plane of the ring; a wavy line ($\sim$) indicates that a substituent may be either in the $\alpha$-configuration or in the $\beta$-configuration or in both, i.e. a mixture thereof.

The radical R, as lower alkyl, is e.g. a branched or straight $C_1$-$C_6$ alkyl group, in particular $C_1$-$C_4$ alkyl, preferably methyl or ethyl.

The present invention relates therefore to a new process for the preparation of compounds of formula (I), as herein defined, the process comprising reacting a compound of formula (II)

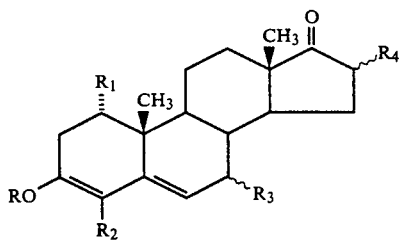

(II)

wherein R, $R_1$, $R_2$, $R_3$ and $R_4$ are as defined above, with a formaldehyde source and an amine of formula (III), or a salt thereof,

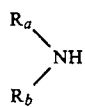

(III)

wherein $R_a$ is lower alkyl and $R_b$ is aryl, so as to obtain a compound of formula (IV)

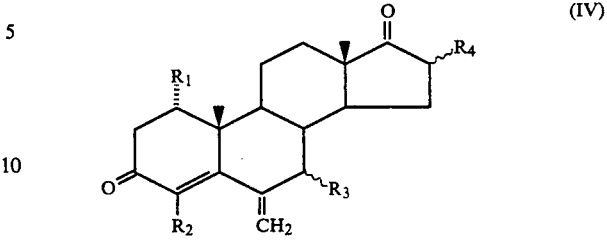

(IV)

wherein $R_1$, $R_2$, $R_3$ and $R_4$ are as defined above, and then dehydrogenating a compound of formula (IV), thus obtained. $R_a$ as lower alkyl is e.g. a branched or straight $C_1$-$C_6$ alkyl radical, in particular $C_1$-$C_4$ alkyl, preferably methyl or ethyl.

$R_b$ as aryl is in particular unsubstituted phenyl or phenyl preferably substituted by a single substituent chosen from $C_1$-$C_4$ alkyl and $C_1$-$C_4$ alkoxy, in particular methyl and methoxy.

Preferred compounds of formula (III) are N-methylaniline and N-ethylaniline.

A salt of a compound of formula (III) is, e.g., a salt with an inorganic acid, preferably a hydrohalic one, in particular hydrochloric acid; or a salt with an organic acid, preferably an alkyl- or aryl- sulphonic acid, in particular p-toluenesulphonic acid.

The reaction of a compound of formula (II) with a formaldehyde source and a compound of formula (III), or a salt thereof, may be carried out in a suitable organic solvent, e.g. tetrahydrofuran, dioxane or a suitable $C_1$-$C_6$ alkanol, e.g. methanol or ethanol.

The reaction is preferably performed by using from about 0.8 to about 2.5 equivalents of a compound of formula (III), or a salt thereof, however 1 to 2 equivalents are more preferred. Any formaldehyde source may be used; however aqueous formaldehyde solutions from about 30 to about 40%, in particular of about 40% are the preferred. The reaction may be performed at a temperature ranging from about 30° to about 50° C., however about 40° C. is the preferred reaction temperature.

The product obtained according to this process, i.e. a compound of formula (IV), may begin to crystallize after cooling the reaction mixture. Crystallization may be completed by treatment with a suitable acidic source, preferably a mineral acid, e.g. sulfonic acid; or a hydrohalic acid, e.g. a hydrochloric acid aqueous solution. Beyond the simple collection by suction, in general further purifications of the product, thus obtained, are not necessary.

Dehydrogenation of a compound of formula (IV), namely introduction of a double bond at the C-1, C-2 position of the steroidal structure, may be carried out according to known methods. For example, when in a compound of formula (IV) $R_1$ is hydrogen, dehydrogenation may be performed by treatment with dichlorodicyanobenzoquinone (DDQ), as disclosed in GB-A2 177 700, but this method has the drawback that DDQ is very expensive and the procedure poorly viable. Therefore we realized an alternative, simple procedure implying a bromination, debromination and dehydrobromination sequence; thence avoiding the use of expensive, low yield dehydrogenating agents, such as DDQ and similar.

The sequence is the following:

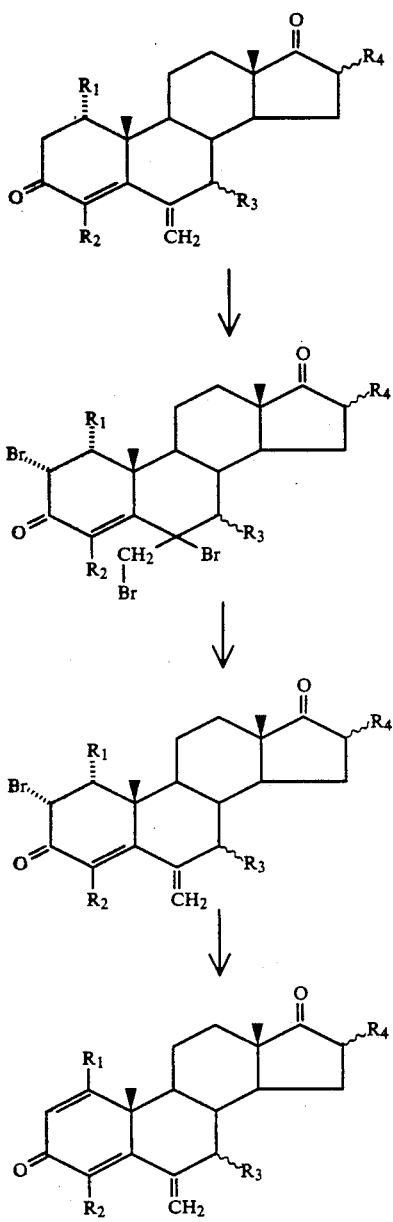

wherein $R_1$, $R_2$, $R_3$ and $R_4$ are as defined above.

According to this scheme the first step involves bromination of a compound of formula (IV) at the C-2 position and on the methylene (i.e. $CH_2=$)moiety. This may be achieved by treatment with a solution of bromine in a suitable orgenic solvent, e.g. a mixture of an anhydrous organic acid, preferably acetic acid, and an ethereal organic solvent, e.g., a di-lower alkyl ether, preferably diethyl ether or methylethylether, or ethylacetate.

A preferred method of performing this step, which leads to compounds of general formula (V), is to add a solution of bromine in concentrated acetic acid to a solution of a compound of formula (II) in diethylether, at a temperature ranging from about 0° C. to about 10° C., over a period of time of from about 10 to about 60 minutes. Generally the tribromide derivative of formula (V) crystallizes on treating the reaction mixture with water. It is then separated by filtration and dried under reduced pressure.

In the debromination step, wich leads to compounds of general formula (VI), the 6-methylene moiety is restored. Debromination of a compound of formula (V) may be carried out by treatment with a suitable alkali metal iodide, i.e. sodium or potassium iodide. The reaction may be performed in an organic ketonic solvent, e.g. a di-lower alkyl ketone, preferably acetone, methyl ethyl ketone or ethyl propyl ketone, at a temperature ranging from about 20° C. to reflux temperature and for reaction times varying from about 10 minutes to about 3 hours. If desired a compound of formula (VI), thus obtained, may be easily separated by the reaction mixture as a pure crystalline material.

The last step of this sequence is the dehydrobromination of a compound of formula (VI), which provides compounds of general formula (I). This elimination reaction may be carried out by reacting a compound of formula (VI), dissolved in a polar solvent, e.g. acetonitrile, dimethylformamide, dimethylsulphoxide, hexamethylenephosphoramide and similar with an inorganic or organic basic agent. An inorganic basic agent may be a mixture of a suitable alkali metal halide with a suitable alkali metal carbonate; preferred examples are mixtures of lithium, sodium or potassium chloride, bromide or iodide with lithium, sodium or potassium carbonate. Preferred examples or organic basic agents are diazabicycloundecene (DBV), diazabicyclononene (DBV), diazabicyclo-ottano (DABCO), pyridine, collidine and the like.

The reaction may be performed at temperatures ranging from about 25° C. to about 150° C., preferably from about 80° C. to about 120° C., and may take from about 30 minutes to about 5 hours. In general the end-product of general formula (I), thus obtained, crystallizes from the cooled reaction mixture after dilution with water and is then separated by filtration.

The compounds of general formula (II), used as starting products in the process according to the present invention, may be obtained according to known methods from compounds of general formula (VII)

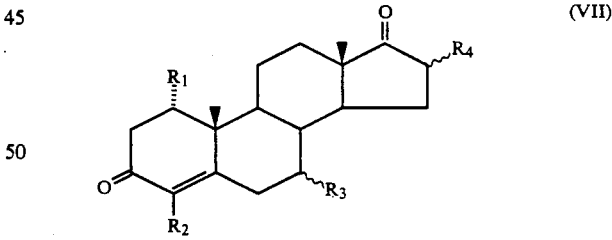

wherein $R_1$, $R_2$, $R_3$ and $R_4$ are as defined above. For example a compound of formula (VII) may be treated with a suitable trialkylorthoformate, preferably trimethylorthoformate, in an inert solvent, e.g. tetrahydrofuran or dioxan, in the presence of an acid catalyst, e.g. p. toluene sulphonic acid, and, if required, of a lower alkanol, preferably ethanol. In a preferred embodiment of the invention a compound of formula (II), thus obtained, is reacted in situ with a formaldehyde source and a compound of formula (III), or a salt thereof, as herein described. The compounds of formula (VII) are known or may be obtained by known methods from known compounds. For example the compound of formula (VII), in which $R_1=R_2=R_3=R_4=H$, i.e. 4-androst- 3,17-dione, is the well known androstendione. Given that the starting compounds of formula (VII) are either commercially available products or easily obtainable from such products and, expecially, that the no column chromatography separation is required, we can state that the process according to the present invention is efficient and amenable to large scale production.

The following Examples illustrate but do not limit the invention.

EXAMPLE 1

6-Methylenandrost-4-ene-3,17-dione[IV,$R_1=R_2=R_3=R_4=H$]

A 1000 ml 4-necked round bottomed flask fitted with a condenser, a thermometer, a dropping funnel and a mechanical stirrer is charged with 20 g of androst-4-ene-3,17-dione, 130 ml of anhydrous tetrahydrofuran, 20 ml of ethanol, 20 ml of triethylorthoformate and 260 mg of p-toluenesulphonic acid and heated at 40° C.

After 1 hr, to this stirred mixture is added a second aliquot of 260 mg of p-toluenesulphonic acid and after 1 hr of additional stirring, there are added 7.8 ml of N-methyl-aniline and 7-10 ml of a 40% formic aldehyde aqueous solution. After 2 hrs of additional stirring at 40° C., the cooled (20° C.) reaction mixture is treated with a dropwise addition of 50 ml of conc. hydrochloric acid. After 1 hr of additional stirring, the reaction mixture is cooled to 0°-5° C., treated with a dropwise addition of 350 ml of cold (5° C.) water and stirred for 1 hr.

The resulting precipitate is filtered with filter aid, washed with water and dried in vacuo at 40° C. There are obtained 14.8 g (73% yield) of the title compound, m.p.: 160°-3° C.

According to the above described procedure and starting from the appropriate precursor of formula (VII) one can prepare also the following compounds:
4-methyl-6-methylenandrost-4-ene-3,17-dione;
4-chloro-6-methylenandrost-4-ene-3,17-dione;
4-bromo-6-methylenandrost-4-ene-3,17-dione; and
4-fluoro-6-methylenandrost-4-ene-3,17-dione.

Analogously one can obtain the following 7- and/or 16- substituted derivatives as single epimers or as a mixture thereof:
7α-methyl-6-methylenandrost-4-ene-3,17-dione; and
16-fluoro-6-methylenandrost-4-ene-3,17-dione.

EXAMPLE 2

2,6-Dibromo-6-bromomethylandrost-4-ene-3,17-dione [V,$R_1=R_2=R_3=R_4=H$]

A 500 ml 3-necked round bottomed flask fitted with a condenser, a thermometer, a dropping funnel and a magnetic stirrer is charged with 4.98 g of 6-methylenandrost-4-ene-3,17-dione, 140 ml of diethyl ether and cooled to 2°-3° C. with an external cooling bath.

To this stirred mixture are added, in the order, 5 drops of a 33% HBr solution in acetic acid, 1.73 ml of Br$_2$ dissolved in 17 ml of glacial acetic acid during 10 min and, after 5 min of additional stirring, a mixture of 25 ml of ethanol and 25 ml of water.

The diethyl ether is evaporated in vacuo and the reaction mixture is treated with 100 ml of water and stirred during 1 hr. The resulting precipitate is filtered with filter aid, washed with water and dried in vacuo at 30°-35° C.

There are obtained 7.6 g (14.15 mmole, 84% yield) of the title compound as white crystals.

According the above described procedure and starting from the appropriate compound of formula (IV) one can prepare also the following compounds:
2,6-dibromo-4-methyl-6-bromomethylandrost-4-ene-3,17-dione;
2,6-dibromo-4-chloro-6-bromomethylandrost-4-ene-3,17-dione;
2,4,6-tribromo-6-bromomethylandrost-4-ene-3,17-dione; and
2,6-dibromo-4-fluoro-6-bromomethylandrost-4-ene-3,17-dione.

Analogously one can obtain the following 7- and/or 16-substituted derivatives as single epimers or as a mixture thereof:
2,6-dibromo-7α-methyl-6-bromomethylandrost-4-ene-3,17-dione; and
2,6-dibromo-16-fluoro-6-bromomethylandrost-4-ene-3,17-dione.

EXAMPLE 3

2-Bromo-6-methylenandrost-4-ene-3,17-dione[VI,$R_1=R_2=R_3=R_4=H$]

A 250 ml 3-necked round bottomed flask fitted with a condenser, a thermometer and a magnetic stirrer is charged with 2.68 g of 2,6-dibromo-6-bromomethyland-rost-4-ene-3,17-dione, 100 ml of acetone and 5.99 g of sodium iodide. The resulting suspension in refluxed for 15 min, cooled to room temperature, filtered and evaporated in vacuo. The residue is taken up with 50 ml of chloroform, washed twice with a saturated sodium thiosulfate aqueous solution, twice with water and dried over anhydrous calcium chloride. Evaporation of the solvent in vacuo yields 1.86 g of the crude title compound which is directly used for the next step.

According to the above described procedure and starting from the appropriate compound of formula (V) one can prepare also the following compounds:
2-bromo-4-methyl-7methylenandrost-4-ene-3,17-dione;
2-bromo-4-chloro-6-methylenandrost-4-ene-3,17-dione;
2,4-dibromo-6-methylenandrost-4-ene-3,17-dione; and
2-bromo-4-fluoro-6-methylenandrost-4-ene-3,17-dione.

Analogously one can obtain the following 7- and/or 16-substituted derivatives as single epimers or as a mixture thereof:
2-bromo-7α-methyl-6-methylenandrost-4-ene-3,17-dione; and
2-bromo-16-fluoro-6-methylenandrost-4-ene-3,17-dione.

EXAMPLE 4

6-Methylenandrosta-1,4-diene-3,17-dione[I,$R_1=R_2=R_3=R_4=H$]

A 100 ml 3-necked round bottomed flask fitted with a condenser, a thermometer and a magnetic stirrer is charged with 1.86 g of crude 2-bromo-6-methylenandrost-4-ene-3,17-dione, 50 ml of anhydrous DMF, 1.84 g of lithium carbonate and 2.11 g of lithium chloride. The reaction mixture is stirred and heated at 120° C. during 2.5 hrs, cooled to room temperature and poured dropwise into a 4-fold volume of stirred water. The resulting precipitate is collected by suction, washed with water and dried in vacuo at 40° C. There are obtained 700 mg (2.36 mmole, 47% yield based on the compound of formula V) of the title compound, m.p.: 192°-5° C.

Found C 81.01; H 8.16. $C_{20}H_{24}O_2$ requires: C 81.04; H 8.05; U.V. (EtOH, mμ): 247 ($\epsilon=13750$).

NMR (CDCl$_3$, δ): 0.94 (3H,s), 1.17 (3H,s), 5.04 (2H,m), 6.18 (1H, br s), 6.25 (1H,dd), 7.09 (1H,d).

Using the same procedure and starting from the appropriate compound of formula (VI) one can prepare the following end-products:

4-methyl-6-methylenandrosta-1,4-diene-3,17-dione;

Found: C 81.15; H 8.32. C$_{21}$H$_{26}$O$_2$ requires: C 81.25; H 8.44;

4-chloro-6-methylenandosta-1,4-diene-3,17-dione, m.p.: 148°–150° C.;

Found: C 72.40, H 6.91, Cl 10.53; C$_{20}$H$_{23}$ClO$_2$ requires: C 72.61, H 7.01, Cl 10.72

N.M.R. (CDCl$_3$, δ): 0.84 (3H,s), 1.24 (3H,s); 5.13 (1H,s); 6.37 (1H,d); 7.08 (1Hd), MS (m/z): 330.

4-bromo-6-methylenandrosta-1,4-diene-3,17-dione,

Found: C 63.90; H 6.03; Br 21.15. C$_{20}$H$_{23}$BrO$_2$ requires: C 64.00; H 6.18; Br 21.29;

4-fluoro-6-methylenandrosta-1,4-diene-3,17-dione,

Found: C 76.35; H 7.34; F 6.01. C$_{20}$H$_{23}$FO$_2$ requires: C 76.41; H 7.37; F 6.04.

Analogously one can obtain the following 7 -and/or 16-substituted derivatives as single epimers or as a mixture thereof:

7α-methyl-6-methylenandrosta-1,4-diene-3,17-dione.

N.M.R. δ p.p.m.: 0.91 (3H,d); 0.94 (3H,s); 1.16 (3H,s); 4.97 (2H,m); 6.14 (1H,d); 6.27 (1H,d); 7.08 (IH,d).

MS m/Z): 310; and 16-fluoro-6-methylenandrosta-1,4-diene-3,17-dione.

EXAMPLE 5

1α-Methyl-6-methylenandrost-4-ene-3,17-dione [IV, R$_1$=—CH$_3$, R$_2$=R$_3$=R$_4$=H].

With a procedure similar to the one described in Example 1, 3 g of 1α-methylandrost-4-ene-3,17-dione, 3 ml of diethylorthoformate, 80 mg of p-toluenesulphonic acid, 1.1 ml of N-methylaniline and 1,2 ml of a 40% formic aldehyde aqueous solution give 2.34 g (75% yield) of the title compound.

NMR (CDCl$_3$, δ): 0.90 (3H,s); 0.95 (3H,d), 1.20 (3H,s), 4.95 (2H,d), 5.98 (1H,s).

According to the above described procedure and starting from the appropriate precursor of formula (VII) one can prepare also the following compounds:

1α-ethyl-6-methylenandrost-4-ene-3,17-dione;

4-chloro-1α-methyl-6-methylenandrost-4-ene-3,17-dione;

4-bromo-1α-methyl-6-methylenandrost-4-ene-3,17-dione; and 4-fluoro-1α-methyl-6-methylenandrost-4-ene-3,17-dione.

Analogously one can obtain the following 7-and/or 16-substituted derivatives as single epimers or as a mixture thereof:

1α,7-dimethyl-16-fluoro-6-methylenandrost-4-ene-3,17-dione; and

1α,7-dimethyl-6-methylenandrost-4-ene-3,17-dione.

EXAMPLE 6

1α-Methyl-2,6-dibromo-6-bromomethylandrost-4-ene-3,17-dione [V, R$_1$=—CH$_3$, R$_2$=R$_3$=R$_4$=H]

With a procedure similar to the one described in Example 2, 1.79 g of 1α-methyl-6-methylenandrost-4-ene-3,17-dione and 0.7 ml of Br$_2$ dissolved in glacial acetic acid give 2.5 g (81% yield) of the title compound as white crystals.

According to the above described procedure and starting from the appropriate precursor of formula (IV) one can prepare also the following compounds:

1α-methyl-2,6-dibromo-6-bromomethylandrost-4-ene-3,17-dione;

1α-methyl-4-chloro-2,6-dibromo-6-bromomethylandrost-4-ene-3,17-dione;

1α-methyl-2,4,6-tribromo-6-bromomethylandrost-4-ene-3,17-dione; and

1α-methyl-4-fluoro-2,6-dibromo-6-bromomethylandrost-4-ene-3,17-dione.

Analogously one can obtain the following 7-and/or 16-substituted derivatives as single epimers or as a mixture thereof:

1α,7-dimethyl-2,6-dibromo-16 fluoro-6-bromomethylandrost-4-ene-3,17-dione; and

1α,7-dimethyl-2,6-dibromo-6-bromomethylandrost-4-ene-3,17-dione.

EXAMPLE 7

1α-Methyl-2-bromo-6-methylenandrost-4-ene-3,17-dione [VI, R$_1$=CH$_3$, R$_2$=R$_3$=R$_4$=H]

With a procedure similar to the one described in the Example 3, 2.5 g of 1α-methyl-2,6-dibromo-6-bromomethylandrost-4-ene-3,17-dione and 5.5 g of sodium iodide in acetone give 1.6 g of the crude title compound which is directly used for the next step.

According to the above described procedure and starting from the appropriate compound of formula (V) one can prepare also the following compounds:

1α-methyl-2-bromo-6-methylenandrost-4-ene-3,17-dione;

1α-methyl-2-bromo-4-chloro-6-methylenandrost-4-ene-3,17-dione;

1α-methyl-2,4-dibromo-6-methylenandrost-4-ene-3,17-dione; and

1α-methyl-2-bromo-4-fluoro-6-methylenandrost-4-ene-3,17-dione.

Analogously one can obtain the following 7-and/or 16 substituted derivatives as single epimers or as a mixture thereof.

1α,7-dimethyl-2-bromo-16fluoro-6-methylenandrost-4-ene-3,17-dione; and

1α,7-dimethyl-2-bromo-6-methylenandrost-4-ene-3,17-dione.

EXAMPLE 8

1-Methyl-6-methylenandrosta-1,4-diene-3,17-diene 3,17-dione [I, R$_1$=CH$_3$, R$_2$=R$_3$=R$_4$=H]

With a procedure similar to the one described in the Example 4, 1.6 g of crude 1α-methyl-2-bromo-6-methylenandrost-4-ene-3,17-dione, 1.6 g of lithium carbonate and 2 g of lithium chloride in DMF give 625 mg of the title compound, m.p.: 158°–161° C.

Found C 80.23; H 8.34. C$_{21}$H$_{26}$O$_2$ requires: C 81.25; H 8.44.

NMR (C DCl$_3$, δ): 0.93 (3H, s), 1.27 (3H, s), 2,13 (3H, d), 4.97 (2H, m), 6.10 (1H, d), 6.20 (1H, m).

Using the same procedure and starting from the appropriate compound of formula (VI) one can prepare the following end-products:

1-ethyl-6-methylenandrosta-1,4-diene-3,17-dione,

Found: C 81.32; H 8.62. C$_{22}$H$_{28}$O$_2$ requires: C 81.44; H 8.70;

1-methyl-4-chloro-6-methylenandrosta-1,4-diene-3,17-dione;

1-methyl-4-bromo-6-methylenandrosta-1,4-diene-3,17-dione; and 1-methyl-4-fluoro-6-methylenandrosta-1,4-diene-3,17-dione, Found: C 76,75; H 7.62; F 5.71. $C_{21}H_{25}FO_2$ requires: C 76.80; H 7.67; F 5.79.

Analogously one can obtain the following 7- and/or 16- substituted derivatives as single epimers or as a mixture thereof.

1,7-dimethyl-16-fluoro-6-methylenandrosta-1,4-diene-3,17-dione;

Found: C 77.05, H 7.80, F 5.45. $C_{22}H_{27}FO_2$ requires: C 77.16, H 7.95, F 5.55.

1-methyl-16-fluoro-6-methylenandrosta-1,4-diene-3,17-dione; and 1,7 dimethyl-6-methylenandrosta-1,4-diene-3,17-dione.

We claim:

1. A process for the preparation of the compound of formula (I)

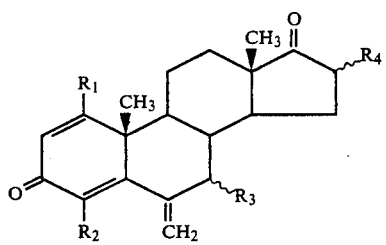

wherein each of $R_1$ and $R_3$, independently, is hydrogen or $C_1$-$C_6$ alkyl; $R_2$ is hydrogen, halogen or $C_1$-$C_6$ alkyl, and $R_4$ is hydrogen or fluorine; the process comprising reacting a compound of formula (II)

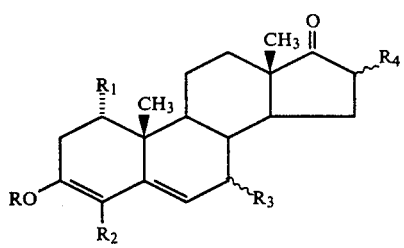

wherein $R_1$, $R_2$, $R_3$, and $R_4$, are defined above and R is a lower alkyl group, with a 30% to 40% aqueous formaldehyde solution and to 1 to 2 equivalents of the hydrohalic salt of an amine of formula (III),

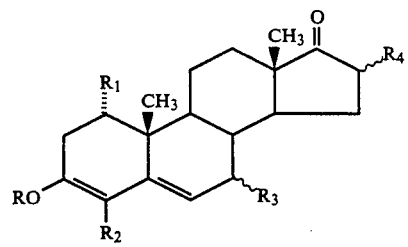

wherein $R_a$ is lower alkyl and $R_b$ is aryl in an organic solvent, at a temperature ranging from 30° C. to 50° C., so as to obtain a compound of formula (IV)

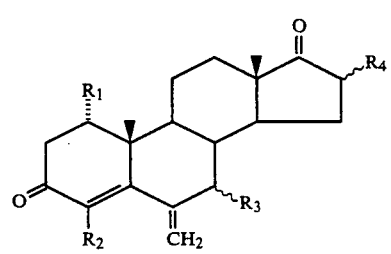

wherein $R_1$, $R_2$, $R_3$, and $R_4$, are defined above and then dehydrogenating a compound of formula (IV), thus obtained.

2. A process according to claim 1, wherein the dehydrogenation of a compound of formula (IV) is performed by bromination of the compound of formula (IV) with bromine, in an organic solvent, at a temperature ranging from 0° C. to 10° C., to obtain a compound of formula (V):

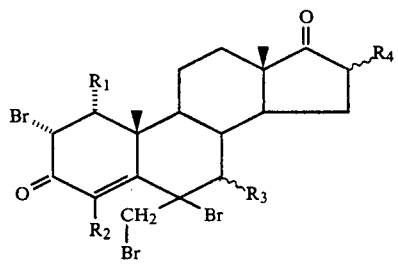

wherein $R_1$, $R_2$, $R_3$, and $R_4$, are defined as in claim 1; debrominating the compound of formula (V) by reaction with an alkali metal iodide, in an organic ketonic solvent, to obtain compound of formula (VI):

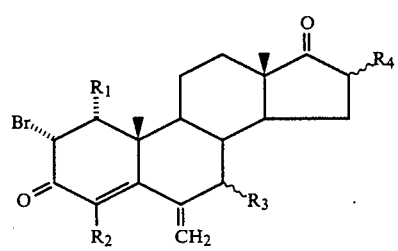

wherein $R_1$, $R_2$, $R_3$, and $R_4$, are defined above, and dehydrobrominating the compound of formula (VI) by reaction with a basic agent, in a polar solvent, to obtain the compound of formula (I).

* * * * *

UNITED STATES PATENT AND TRADEMARK OFFICE
CERTIFICATE OF CORRECTION

PATENT NO. : 4,990,635

DATED : February 5, 1991

INVENTOR(S) : Antonio LONGO et al

It is certified that error appears in the above-identified patent and that said Letters Patent is hereby corrected as shown below:

On the cover page, after Item [22], the following should appear:

-- [30]     Foreign Application Priority Data
     Jan. 26, 1988 [GB]   Great Britain . . . . 8801697 --.

Signed and Sealed this

Twenty-fourth Day of November, 1992

*Attest:*

DOUGLAS B. COMER

*Attesting Officer*     *Acting Commissioner of Patents and Trademarks*

UNITED STATES PATENT AND TRADEMARK OFFICE
CERTIFICATE OF CORRECTION

PATENT NO. : 4,990,635  
DATED : February 5, 1991  
INVENTOR(S) : LONGO et al

It is certified that error appears in the above-identified patent and that said Letters Patent is hereby corrected as shown below:

On the cover page, item [56], "Buzzett" should read -- Buzzetti --;

Col. 12, please delete formula (III) and substiture therefor new formula (III) below.

--  --.

Signed and Sealed this

Twenty-fifth Day of May, 1993

Attest:

MICHAEL K. KIRK

Attesting Officer

Acting Commissioner of Patents and Trademarks